(12) United States Patent  (10) Patent No.: US 8,505,543 B2
Miller                     (45) Date of Patent:     Aug. 13, 2013

(54) MALE CHASTITY APPARATUS, SYSTEM, AND METHOD

(75) Inventor: A. Frank Miller, Wellington, UT (US)

(73) Assignee: A.L. Enterprises, Inc., Las Vegas, NV (US)

( * ) Notice: Subject to any disclaimer, the term of this patent is extended or adjusted under 35 U.S.C. 154(b) by 557 days.

(21) Appl. No.: 12/704,691

(22) Filed: Feb. 12, 2010

(65) Prior Publication Data

US 2010/0200004 A1    Aug. 12, 2010

Related U.S. Application Data

(60) Provisional application No. 61/152,195, filed on Feb. 12, 2009.

(51) Int. Cl.
*A01K 15/04* (2006.01)
*A01K 21/00* (2006.01)
*A61F 5/37* (2006.01)
*A61F 13/00* (2006.01)
*A61F 5/48* (2006.01)
*A61B 19/00* (2006.01)

(52) U.S. Cl.
USPC ........... 128/883; 128/846; 128/869; 128/885; 119/814; 119/838; 600/34; 600/39; 600/40; 600/41

(58) Field of Classification Search
USPC ............. 128/846, 869, 883, 885; 600/38–41; 119/814, 838
See application file for complete search history.

(56) References Cited

U.S. PATENT DOCUMENTS

| | | |
|---|---|---|
| 397,106 A | 2/1889 | Bowen |
| 826,377 A | 7/1906 | Sonn |
| 934,240 A | 9/1909 | Tunnessen |
| 997,067 A | 7/1911 | Lang |
| 1,215,028 A | 2/1917 | Jones |
| D90,678 S | 9/1933 | Parke |
| 2,468,580 A | 4/1949 | Weis et al. |
| D213,154 S | 1/1969 | Allen |
| 3,648,700 A | 3/1972 | Warner |
| 4,014,044 A | 3/1977 | Figueroa et al. |
| 4,164,217 A | 8/1979 | Schrock |
| 4,599,751 A | 7/1986 | Bouwhuis |
| 5,163,447 A | 11/1992 | Lyons |
| 5,192,271 A | 3/1993 | Kalb et al. |

(Continued)

OTHER PUBLICATIONS

Chastity Devices CB3000.Sensual Pleasures, URL:http//web.archive.org/web/200604271404/http://www.cb3000.html> [Retrieved from the Internet on Jul. 28, 2008].

(Continued)

*Primary Examiner* — Patricia Bianco
*Assistant Examiner* — Brandon L Jackson
(74) *Attorney, Agent, or Firm* — Durham, Jones & Pinegar Intellectual Property Law Group (57) ABSTRACT

A male chastity apparatus, system and method are disclosed. The apparatus, in one embodiment, includes a housing, a protrusion, and a lock. The housing is configured to contain a shaft of a penis of a user. The housing, in certain embodiments, is made of a substantially rigid material that prevents the user from stimulating the shaft of the user's penis. The protrusion is configured to engage a piercing in the user's penis. The protrusion, in certain embodiments, is also made of a substantially rigid material. The lock is configured to engage the protrusion and to attach the protrusion to the housing.

20 Claims, 10 Drawing Sheets

(56) References Cited

U.S. PATENT DOCUMENTS

| | | |
|---|---|---|
| D335,938 S | 5/1993 | Kam |
| 5,238,009 A | 8/1993 | House |
| D339,418 S | 9/1993 | Flynn |
| 5,353,811 A | 10/1994 | Davis et al. |
| 5,368,050 A | 11/1994 | Donelan |
| 5,388,580 A | 2/1995 | Sullivan et al. |
| 5,485,636 A | 1/1996 | Yandell |
| D368,140 S | 3/1996 | Hopper |
| 5,524,638 A | 6/1996 | Lyons |
| D384,156 S | 9/1997 | Kain |
| 5,713,830 A | 2/1998 | Tucker et al. |
| 5,752,933 A | 5/1998 | Morrison |
| 5,845,642 A | 12/1998 | Vanmoor |
| 5,899,875 A | 5/1999 | Millot et al. |
| D417,502 S | 12/1999 | Johnson |
| 6,033,374 A | 3/2000 | Miller, Jr. |
| 6,090,088 A | 7/2000 | Nichols |
| D433,756 S | 11/2000 | Castillo |
| 6,203,491 B1 | 3/2001 | Uribe |
| D441,082 S | 4/2001 | Ruscitti |
| D459,469 S | 6/2002 | Johnson |
| D460,172 S | 7/2002 | Johnson |
| D466,218 S | 11/2002 | Dalton et al. |
| 6,736,142 B2 | 5/2004 | Sanchez Gomez |
| D536,458 S | 2/2007 | Nan |
| D558,356 S | 12/2007 | Nan |
| D571,047 S | 6/2008 | Kamradt |
| 7,578,296 B2 | 8/2009 | Miller et al. |
| 8,216,258 B2 * | 7/2012 | Skipper .................. 606/151 |
| 2002/0033179 A1 | 3/2002 | Burgos |
| 2003/0024536 A1 | 2/2003 | Bagby |
| 2003/0056798 A1 | 3/2003 | Sanchez Gomez |
| 2003/0136415 A1 | 7/2003 | Lanton, Jr. |
| 2004/0094163 A1 | 5/2004 | Benson |
| 2005/0124854 A1 | 6/2005 | Suchy et al. |
| 2008/0127986 A1 | 6/2008 | Miller |

OTHER PUBLICATIONS

CB-2000-Lether & Lingerie- Lingerie, Male Chastity Devices & Adult Novelties [online], Oct. 31, 2004 [retrieved Oct. 23, 2008]. Retrieved from the Internet <http://web.archive.org/web.cb-2000.com/cb3000.html>.

CB-6000.com World Leader in Male Chastity, http://www.cb-6000.com, [retrieved from the internet on Dec. 17, 2010].

* cited by examiner

MALE CHASTITY APPARATUS, SYSTEM, AND METHOD

CROSS-REFERENCES TO RELATED APPLICATIONS

This application claims priority to U.S. Provisional Patent Application No. 61/152,195 entitled "Male Chastity Apparatus, System, and Method" and filed on Feb. 12, 2009 for A. Frank Miller, which is incorporated herein by reference.

BACKGROUND

1. Field of the Invention

This invention relates to chastity devices, and more particularly to male chastity apparatuses, methods, and systems.

2. Description of the Related Art

Chastity devices have a long and storied history, some forms of them dating back millennia. While female chastity devices are more common, male chastity devices have also been manufactured and used for some time. Generally, a device of this type is installed and locked onto a man's genitals, with the key or other device or method for unlocking it generally being held by the man's sexual partner, ensuring that the man engages in no sexual activity except with the key holder.

Female chastity devices are generally easier to conceive of and manufacture than their male counterparts, since they have the relatively simple goal of preventing penetration and deal with the relatively simple external female anatomy. Male chastity devices, at least effective ones, have proven to be more difficult to create given the external nature of male genitalia. Due to the external nature of the male genitalia, the utility of the prior art devices has been circumvented by the wearer of the devices. Further, prior art devices have often proven to be wildly complicated, requiring belts, straps, harnesses, even rigid pants and suspenders. They often require large, unwieldy attachments to the penis and testicles, making them cumbersome and unsightly—even beneath clothing. Further complications arise from the need to provide an outlet for urination.

SUMMARY

From the foregoing discussion, it should be apparent that a need exists for an apparatus, system, and method that is effective, unobtrusive, and comfortable for the user. Beneficially, such an apparatus, system, and method would provide a secure and reliable mechanism for attaching the device to the user.

The present invention has been developed in response to the present state of the art, and in particular, in response to the problems and needs in the art that have not yet been fully solved by currently available male chastity devices and systems. Accordingly, the present invention has been developed to provide an apparatus, system, and method for male chastity that overcome many or all of the above-discussed shortcomings in the art.

The apparatus, in one embodiment, includes a housing, a protrusion, and a lock. The housing is configured to contain a shaft of a penis of a user. The housing, in certain embodiments, is made of a substantially rigid material that prevents the user from stimulating the shaft of the user's penis. The protrusion is configured to engage a piercing in the user's penis. The protrusion, in certain embodiments, is also made of a substantially rigid material. The lock is configured to engage the protrusion and to rigidly attach the protrusion to the housing.

In certain embodiments a distal end of the protrusion is shaped as a partial ring having a radius sufficient to clear an end of a glans of a user's penis when the protrusion is engaged in a user's Prince Albert piercing.

In a further embodiment, the housing includes a recess configured to receive a proximal end of the protrusion. In one embodiment the proximal end of the protrusion includes an insertion member configured to engage the recess of the housing.

In another embodiment, a cross section of the insertion member is substantially oval shaped. A cross section of the insertion member of the protrusion is also substantially oval shaped. In such an embodiment any rotation of the protrusion is minimized when the insertion member is disposed within the recess.

In one embodiment the apparatus also includes a lock lobe disposed on the housing. The recess may communicate with the lock lobe such that the insertion member of the protrusion is at least partially disposed within the lock lobe. In a further embodiment, the insertion member includes a slot transecting the insertion member. The lock lobe may also include a slot that coincides with the slot on the insertion member. The lock includes a locking flange configured to engage the lock lobe through the slot in the lock lobe and the slot on the insertion member. The flange may be configured to rotate radially from a first position, in which the flange engages the slot of the insertion member, to a second position, in which the flange disengages the slot of the insertion member.

In certain embodiments the housing includes a flange extending from a bottom of the housing. In one embodiment the flange may be configured to support a tip of the user's penis. In another embodiment the flange engages the protrusion at a distal end of the protrusion. In this manner the distal end of the protrusion and the flange cooperate to prevent unauthorized removal of the housing from the shaft of the user's penis.

In a further embodiment, a top of the housing is shorter than a bottom of the housing. A distal end of the housing may be sloped from the bottom of the housing to the top of the housing and may be contoured to the shape of a glans of the user's penis.

In one embodiment, the male chastity apparatus includes an extension ring configured to engage the housing to extend the length of the housing.

A method of the present invention is also presented for facilitating male chastity. The method in the disclosed embodiments substantially includes the steps necessary to carry out the functions presented above with respect to the operation of the described apparatus and system. In one embodiment, the method includes placing a housing on a shaft of a penis of a user, placing a protrusion through a piercing in the user's penis, inserting the protrusion in a recess disposed in the housing, and locking the protrusion in the recess of the housing with a lock. The method also may include extending the length of the housing by adding an extension ring to an end of the housing.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a detailed description of the invention will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 1:
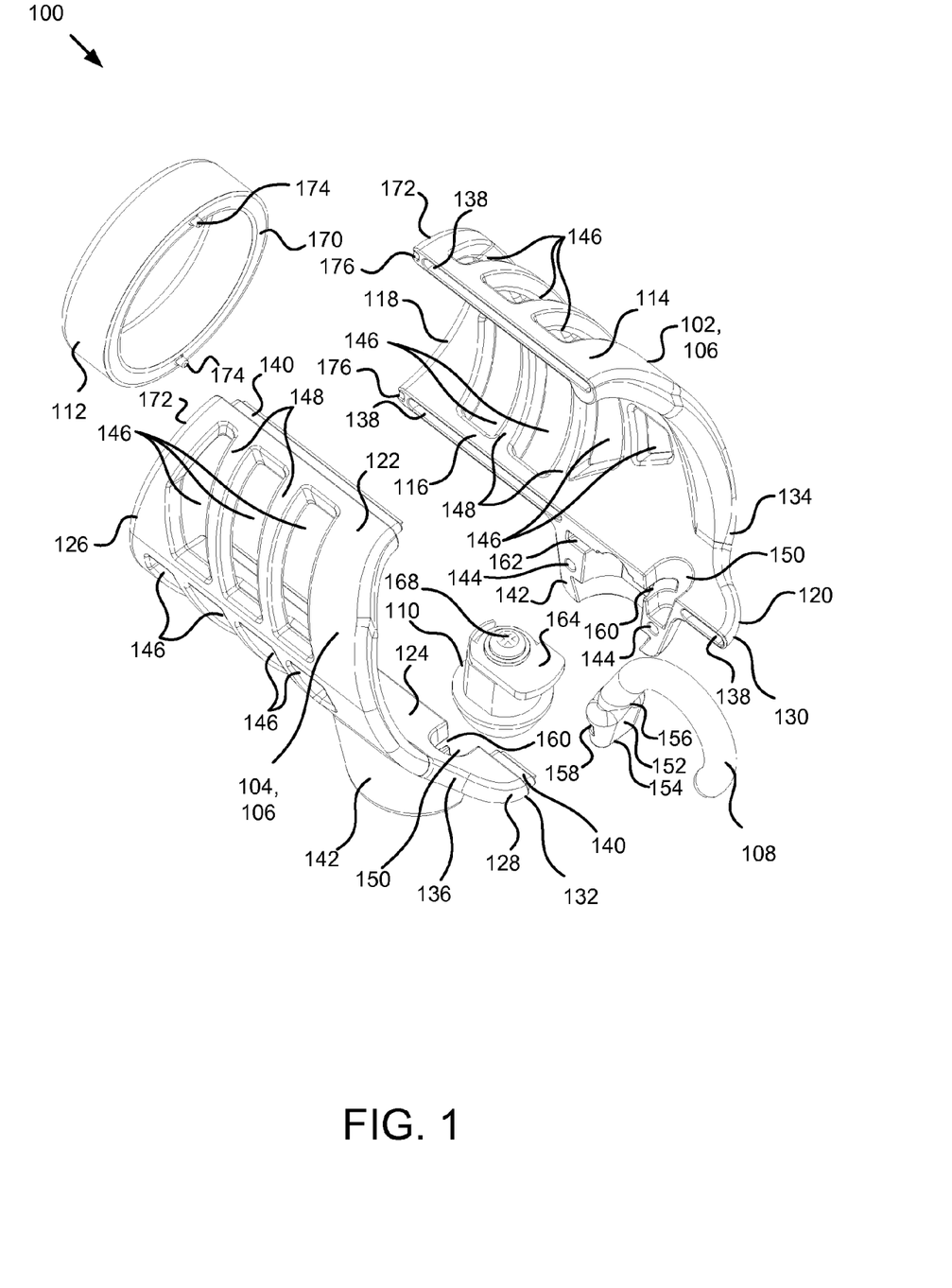
FIG. 1 is an exploded view illustrating one embodiment of a male chastity device in accordance with the present invention.

FIG. 1 depicts an exploded view of a male chastity apparatus 100 according to one embodiment of the present invention. The male chastity apparatus 100 includes a first housing section 102 and a second housing section 104 (collectively housing 106). The male chastity apparatus 100 also includes a protrusion 108, a lock 110, and an extension ring 112.

The housing 106 comprises an at least partial enclosure elongated in a lengthwise direction and configured to encompass at least a portion of a shaft of a user's penis to prevent manual stroking of the shaft of the penis by the user. In the embodiment illustrated in FIG. 1, the housing is made of two semicircular housing sections 102 and 104. The two semicircular housing sections 102 and 104 are combined to create a cylinder through which the user's penis is placed. The first housing section 102 has a top 114, a bottom 116, proximal end 118 and a distal end 120. The second housing section 104 has a top 122, a bottom 124, a proximal end 126, and a distal end 128. In certain embodiment the first housing section 102 and the second housing section 104 are mirror images of each other.

In certain embodiments the top 114 of the first housing section 102 and the top 122 of the second housing section 104 are substantially shorter than the bottom 116 of the first housing section 102 and the bottom 124 of the second housing section 106. The distal ends 120 and 128 of the first and second housing sections 102 and 104 are sloped from the bottoms 120 and 128 to the tops 114 and 122 of the first and second housing sections 102 and 104 respectively to accommodate the glans of the user's penis. Thus, in certain embodiments the distal ends 120 and 128 of the first and second housing sections 102 and 104 are shaped to contour to the glans of the user's penis. In certain embodiments the distal ridge 134 of the first housing section 102 and the distal ridge 136 of the second housing section 104 are smooth. By contouring the distal ends 120 and 128 of the housing 106 to the glans of the user's penis and providing smooth distal ridges 134 and 136, the housing 106 provides the user a comfortable experience when wearing the male chastity apparatus 100. Additionally, in certain embodiments, when applying the male chastity apparatus 100 to the user's penis, the end of the user's penis is manipulated to allow a protrusion 108 through a Prince Albert piercing located on the underside of the user's penis just behind the glans of the user's penis. By having a relatively shorter top 122 than a bottom 124, the housing 106 allows the user to roll the glans of the user's penis back to access the user's Prince Albert piercing.

In certain embodiments the first and second housing sections 102 and 104 have flanges 130 and 132 located at the distal ends 120 and 122 thereof. In one embodiment the flange 130 and the flange 132 are sized to support the tip of the user's glans when the user is wearing the male chastity apparatus 100. In certain embodiments the flange 130 and the flange 132 are sized to cooperate with the protrusion 108 to prevent the unauthorized removal of the male chastity apparatus 100. Thus, in certain embodiments the protrusion 108 contacts the flanges 130 and 132. As discussed below, the protrusion 108 is received within a recess 150 at the bottom end 154 of the protrusion 108. Where the end of the protrusion 108 opposite the bottom end 154 is in contact with the flanges 130 and 132 of the housing 106, the protrusion 108 and the flanges 130 and 132 operate to trap the skin of a user's Prince Albert piercing between the ends of the protrusion 108 preventing the unauthorized removal of the male chastity apparatus 100.

The first housing section 102 has recesses 138 that receive tabs 140 on the second housing section 104. The tabs 140 align the first housing section 102 with the second housing section 104 when the tabs 140 are received within the recesses 138. In certain embodiments the tabs 140 are used to weld the first housing section 102 to the second housing section 104. Additional recesses 144 located on the lock lobe 142 of the first housing section 114 may receive corresponding tabs (not shown) on the lock lobe 142 of the second housing section 122 for connecting smaller areas on the first and second housing sections 114 and 122 respectively. One of skill in the art will recognize that any method of welding the first housing section 102 to the second housing section 104, such as hot gas welding, speed tip welding, extrusion welding, contact welding, hot plate welding, high frequency welding, ultrasonic welding, vibration welding, spin welding, laser welding, solvent welding, or the like may be used to connect the first housing section 102 to the second housing section 104. In other embodiments the first housing section 102 may be glued to the second housing section 104. In another embodiment, the entire housing 106 may be extrusion molded into a single unit. One of skill in the art will recognize that where the housing 106 is extrusion molded, the lock lobe 142 may be omitted from the extruded housing 106. In such an embodiment, a separate lock lobe 142 may be created and affixed to the housing 106 after both the housing 106 and the lock lobe 142 have been created. One of skill in the art will recognize that the plastic components of the male chastity apparatus, such as the housing 106, protrusion 108, and extension ring 112 may be created by any available form of plastic molding such as injection molding, rotation molding or the like. In one embodiment the entire male chastity apparatus 100 may be made of metal or other solid material.

In one embodiment the two housing sections 102 and 104 maybe constructed such that the tops 114 and 122 of the first and second housing sections 102 and 104 are spaced at some distance apart when the housing sections 102 and 104 are combined to form the housing 106. The bottoms 116 and 124 of the first and second housing sections 102 and 104 may be constructed to maintain a gap between the tops 114 and 122 of the first and second housing sections 102 and 104. In an alternate embodiment, the bottoms 116 and 124 of the first and second housing sections 102 and 104 may be spaced apart when the housing sections 102 and 104 are combined to form the housing 106. In such embodiments the distance between first and second housing sections 102 and 104 may be such that the user cannot remove the penis from the complete housing 106 when the user is wearing the male chastity apparatus 100. The space between the first housing section 102 and the second housing section 104 may be wide enough to insert a cleaning utensil such as a cotton swab or small brush while still maintaining the user's penis within the housing 106.

Access vents 146 provide a user access to the shaft of the penis while the user is wearing the chastity apparatus 100 for hygienic purposes. Support struts 148 maintain rigidity of the male chastity apparatus 100 to prohibit unauthorized stimulation of the user's penis. The access vents 146 may be sized and configured to prohibit stimulation of the shaft of the user's penis while still being large enough to allow access with a cleaning utensil such as a cotton swab or small brush. The access vents 146 also allow air circulation through the housing 106 while the user is wearing the male chastity device 100. One of skill in the art will recognize that the access vents 146 may be shaped in different configurations other than those depicted in the accompanying FIGS. In one embodiment the access vents 146 allow access to the shaft of the user's penis for cleansing while prohibiting stimulation of the shaft of the user's penis. In certain embodiments the air circulation through access vents 146 prevent excess sweating which may limit irritation of the user's penis.

In certain embodiments the housing 106, made up of the first housing section 102 and the second housing section 104, may be sized to accommodate the shaft of a user's penis. One of skill in the art will recognize that the male anatomy is typically not uniform across the general public. Therefore, in certain embodiments the housing 106 may be commercially offered in a number of sizes to fit a particular user's penis. In one embodiment the housing 106, when worn by a user, may encompass the shaft of a user's penis and may be in constant contact with the circumference of the shaft of the user's penis. In another embodiment, the housing 106 may encompass the shaft of the user's penis and leave a one eight inch gap between the inner diameter of the housing 106 and the shaft of the user's penis. In certain embodiments a one eight inch to a one fourth inch gap between the housing 108 and the shaft of the user's penis may be created by stretching the user's penis away from the user's body. Such a gap may be desirable, in certain embodiments, for hygienic purposes and to allow access for cleaning the shaft of the user's penis.

The first housing section 104 and the second housing section 106 each contain one half of a recess 150 that form a complete recess 150 when the first housing section 102 and the second housing section 104 are connected to each other. The recess 150 receives an insertion member 152 on the protrusion 108. In certain embodiments the recess 150 is tapered from top to bottom with the insertion member 152 correspondingly tapered from top to bottom. That is, the top end 156 of the insertion member 152 is relatively larger than the bottom end 154 of the insertion member 152. By tapering the recess 150 and the insertion member 152, the recess 150 provides a tight fit around the insertion member 152 as the insertion member 152 is placed further within the recess 150. Because the bottom end 154 of the insertion member 152 is relatively narrower than the top end 156 of the insertion member 152 insertion of the insertion member 152 within the recess 150 is facilitated making insertion of the insertion member 152 into the recess 150 easier for the user.

The insertion member 152 contains a slot 158 that aligns with a slot 160 in the recess 150 when the insertion member 152 is fully inserted within the recess 150. The slot 160 in the recess 150 communicates with the slot 162 in the lock lobe 142 to allow a flange 164 on the lock 110 to move radially through slot 160 in the recess 150 and the slot 162 in the lock lobe 142 from a first position in which the flange 164 engages the slot 158 of the insertion member 152 to a second position in which the flange 164 does not engage the slot 158 of the insertion member 152. When the flange 164 is in the first position, the insertion member 152 and thus the protrusion 108 cannot be removed from the housing 106. The flange 164 is connected to the lock 110 by a screw which allows the flange 164 to rotate within the slots 160 and 162. In the embodiment illustrated in FIG. 1, the lock 110 is depicted as a cam lock. However, one of skill in the art will recognize that other locking mechanisms may be constructed without departing from the spirit of the present invention.

In certain embodiments the lock 110 may be removed from the housing 106 when the male chastity apparatus 100 is not being worn by the user. In other embodiments the lock 110 is integral with the housing 106 and cannot be removed after the first housing section 102 and the second housing section 104 are connected together. In one embodiment the lock 110 is made of a nonferrous metal such as brass. In another embodiment the lock 110 may be made a plastic material. By using a nonferrous metal or plastic as the material for the lock 110, the user can wear the male chastity apparatus 100 without embarrassment when using metal detectors which are commonly found in airport security or in boarding other vessels or locations requiring metal detection for security purposes.

In one embodiment an extension ring 112 may be added to the proximal end 118 of the housing 106 to extend the length of the male chastity apparatus 100 for males having larger genitalia. Additional extension rings 112 may be added as necessary to accommodate the specific length of the user. In one embodiment the extension ring 112 may come in various lengths for a custom fit. In certain embodiments the inner diameter of the housing 106 maybe made available in different sizes to accommodate different girths of the user's penis. Obviously the extension ring 112 may also be made available with different inner diameters corresponding to the inner diameters available for the housing 106.

The extension ring 112 may contain a recess 170 that receives an extension ring alignment flange 172 on the housing. The cooperation between the recess 170 and the extension ring alignment flange 172 may operate to keep the extension ring 112 in place on the housing 106. The extension ring 112 may also contain protrusions 174 that are received within extension ring alignment recesses 176 to stop the extension ring 112 from rotating. One of skill in the art will recognize that any method of connecting the extension ring 112 to the housing 106 is within the scope of this invention. For example, in certain embodiments the recess 170 and the extension ring alignment flange 172 may snap together to hold the extension ring 112 to the housing 106. In another embodiment, only the protrusions 174 and the extension ring alignment recesses 176 are configured to snap together. In certain embodiments the extension ring 112 may be welded to the housing 106. One of skill in the art will recognize that any method of plastic welding may be used to connect the extension ring 112 to the housing 106. Some non-limiting examples of plastic welding that may be used to connect the extension ring 112 to the housing include hot gas welding, speed tip welding, extrusion welding, contact welding, hot plate welding, high frequency welding, ultrasonic welding, vibration welding, spin welding, laser welding, solvent welding, or the like. In other embodiments the extension ring 112 may be glued to the housing 106.

Figure 2A:
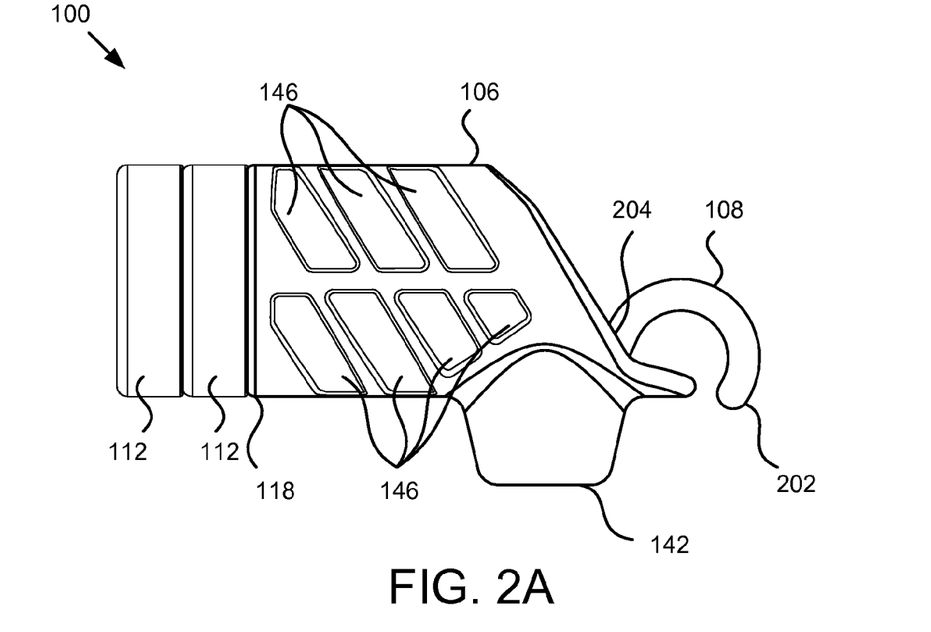
FIG. 2A is a right side view further illustrating one embodiment of the male chastity device of FIG. 1 in accordance with the present invention.
Figure 2B:
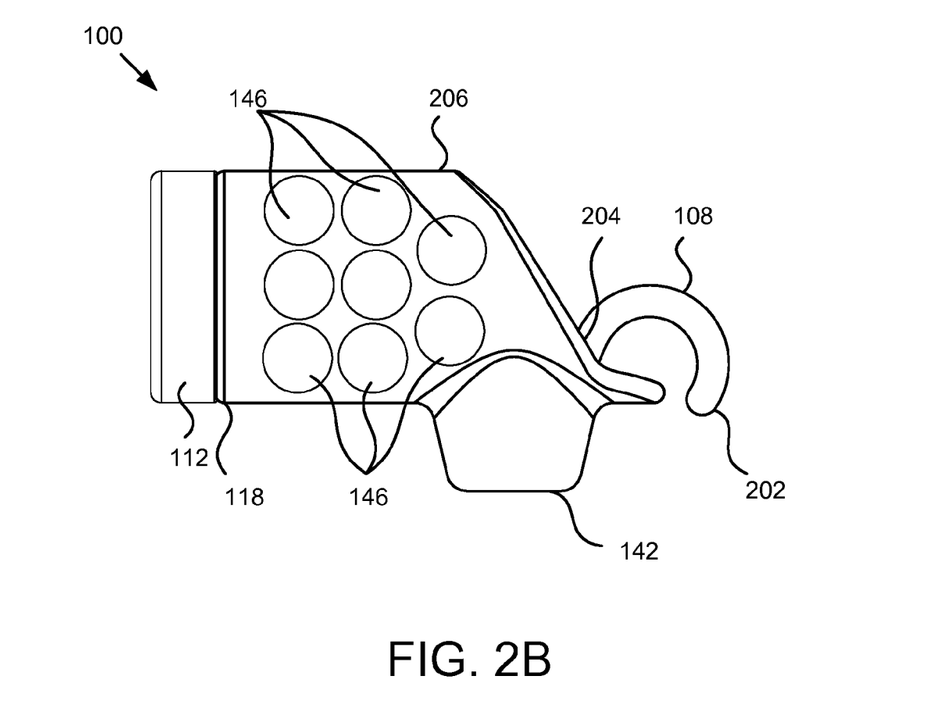
FIG. 2B is a right side view further illustrating another embodiment of the male chastity device of FIG. 1 in accordance with the present invention.

FIG. 2A is a side view of the male chastity apparatus 100 according to one embodiment. The male chastity apparatus depicted in FIG. 2A includes a housing 106, a protrusion 108, and a lock (not shown) disposed within a lock lobe 142. The housing 106 and the protrusion 108 are substantially similar to the housing 106 and the protrusion 108 of FIG. 1 described above. As depicted, the protrusion 108 is received within the recess 150 in the embodiment illustrated in FIG. 2A and 2B. An additional extension ring 112 is connected to the proximal end 118 of the housing 106 to accommodate a user with a longer penis.

In certain embodiments the protrusion 108 may be available in a variety of sizes to accommodate different locations for a user's piercing. For example, a user with a Prince Albert piercing near the end of the glans of his penis can use a protrusion 108 with a relatively small radius. That is the distance between the end of distal end 202 of the protrusion 108 and the proximal end 204 of the protrusion 108 may be relatively shorter than is necessary for a user with a Prince Albert piercing located further back on the glans of the user's penis. This is because the distal end 202 of the protrusion 108 should clear the end of the glans of the user's penis.

One of skill in the art will recognize that the protrusion 108 may be sized and shaped to accommodate other types or locations of male genitalia piercings. For example, in certain embodiments the protrusion 108 comprises a straight bar configured to engage an ampallang piercing wherein the piercing is made horizontally through the glans of the user's penis. A straight protrusion 108 may also be used with an apadravya piercing, a dydoe piercing, or a frenum piercing. One of skill in the art will recognize that an apadrvya piercing is made vertically through the glans of the user's penis and a dydoe piercing is made through the ridge of the user's glans. A frenum piercing is located in the flexible skin of the underside of the shaft just behind the glans of the user's penis or at the base of the shaft.

In the embodiment illustrated in FIG. 2A the access vents 146 are symmetrically spaced along the length of the housing 106. In other embodiments, such as the embodiment illustrated in FIG. 2B the housing 206 may include access vents 146 which are circular or some other shape. In certain embodiments the shape of the access vents 146 may be decorative such as hearts, diamonds or other aesthetically pleasing shapes. As discussed above, the access vents 146 should be large enough to allow cleaning of the shaft of the user's penis and small enough to prohibit stimulation of the penis while the user is wearing the male chastity apparatus 100.

Figure 3:
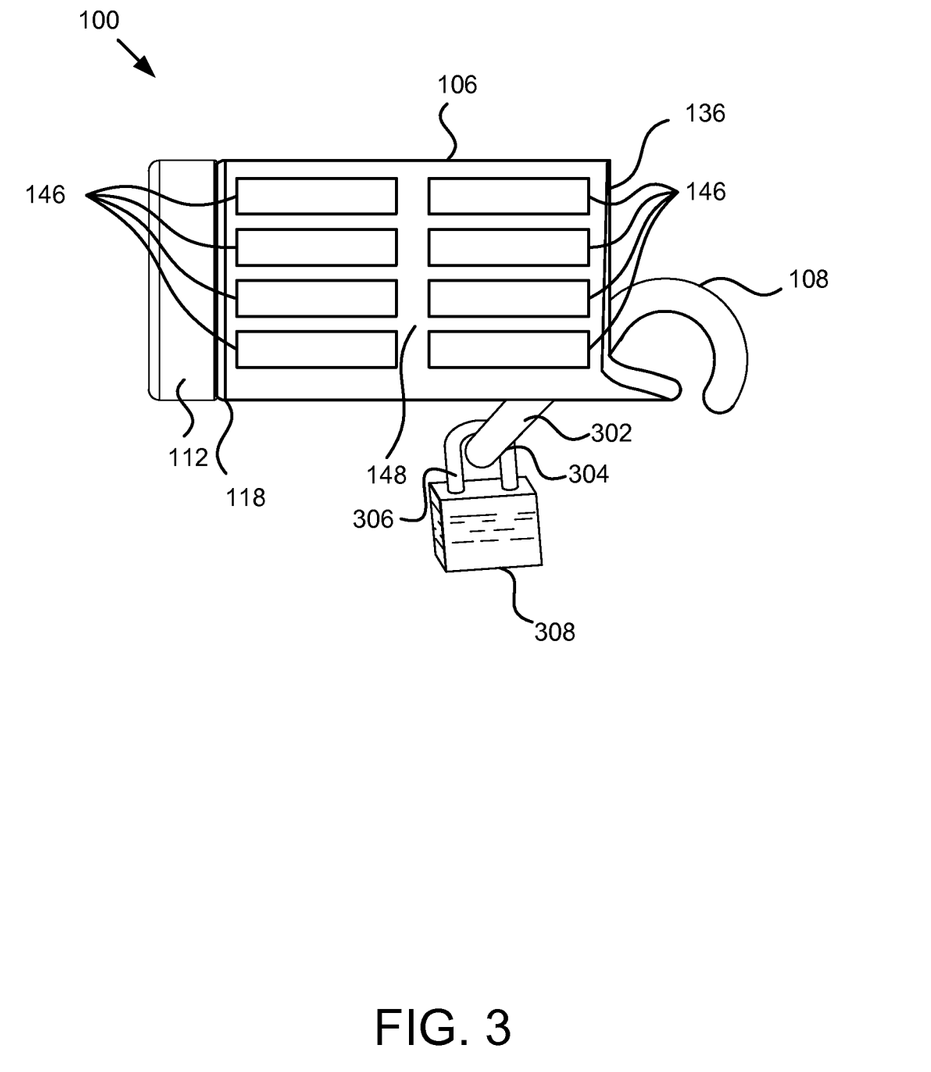
FIG. 3 is a right side view illustrating an embodiment of a locking mechanism for the male chastity device in accordance with the present invention.

FIG. 3 illustrates another embodiment of the male chastity apparatus 100 wherein the distal ridge 136 of the second housing section 104 is not sloped. One of skill in the art will recognize that while the first housing section 102 is not illustrated, the distal ridge 134 of the first housing section 102 may be similarly not sloped.

FIG. 3 illustrates another possible configuration for the access vents 146. In this embodiment, the sizing of the access vents 146 may be controlled to prevent stimulation of the user's penis along the shaft. The access vents 146 are illustrated in two rows with a support strut 148 disposed between the rows. In another embodiment the support strut 148 may be omitted with the access vents 146 running the entire length of the housing 106.

In the embodiment illustrated in FIG. 3, the lock lobe 142 is omitted and the protrusion 108 is configured to be inserted all the way through the housing 106 with a locking portion 302 of the protrusion 108 extending below the housing 106. The locking portion 302 of the protrusion 108 may contain a hole 304 for receiving the shackle 306 of a lock 308.

Figure 4:
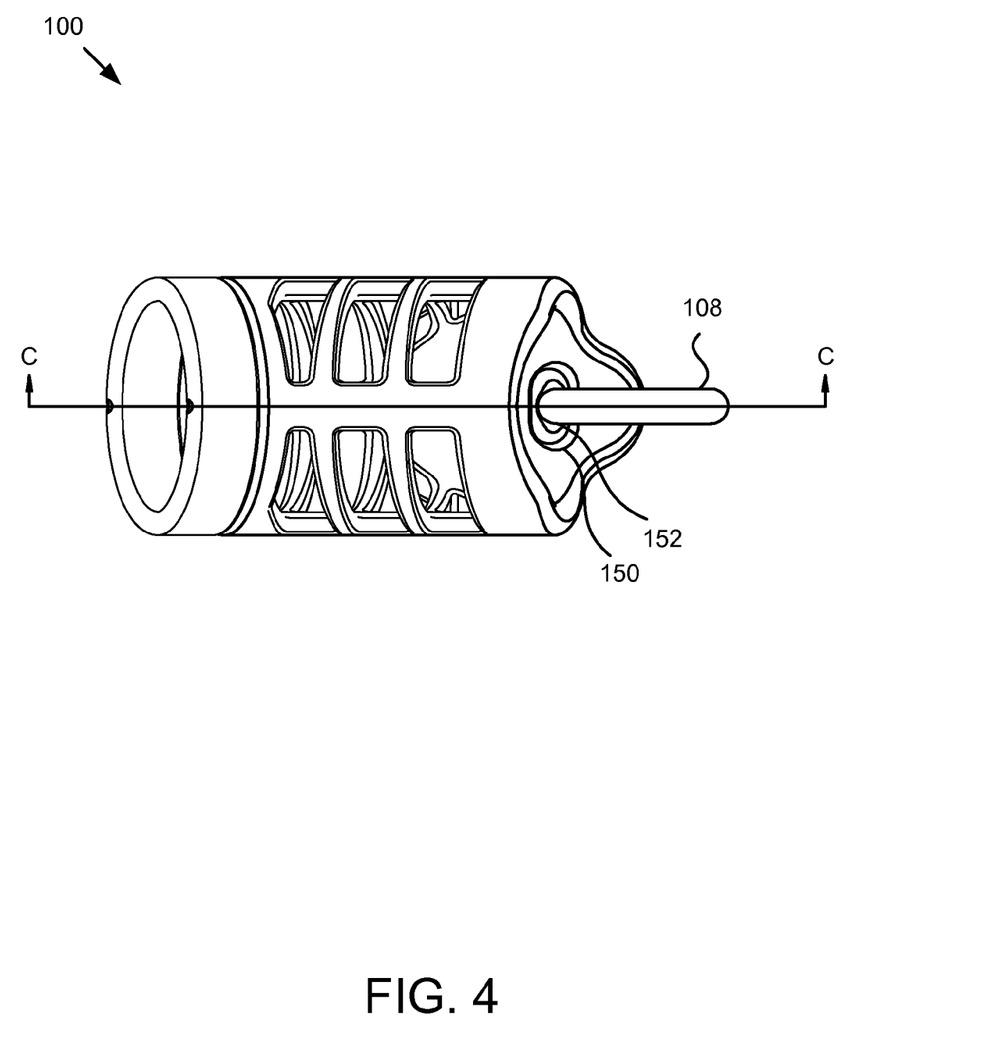
FIG. 4 is a top view illustrating one embodiment of the male chastity device in accordance with the present invention

FIG. 4 illustrates a top view of the male chastity apparatus 100 showing the protrusion 108 disposed within the recess 150. In certain embodiments both the recess 150 and the insertion member 152 are substantially oval shaped. By making the recess 150 and the insertion member 152 oval shaped, when the insertion member 152 is disposed within the recess 150, the rotation of protrusion 108 is minimized. One of skill in the art will recognize that the insertion member 152 and the recess 150 may include other shapes configured to reduce rotation of the protrusion 108.

Figure 5:
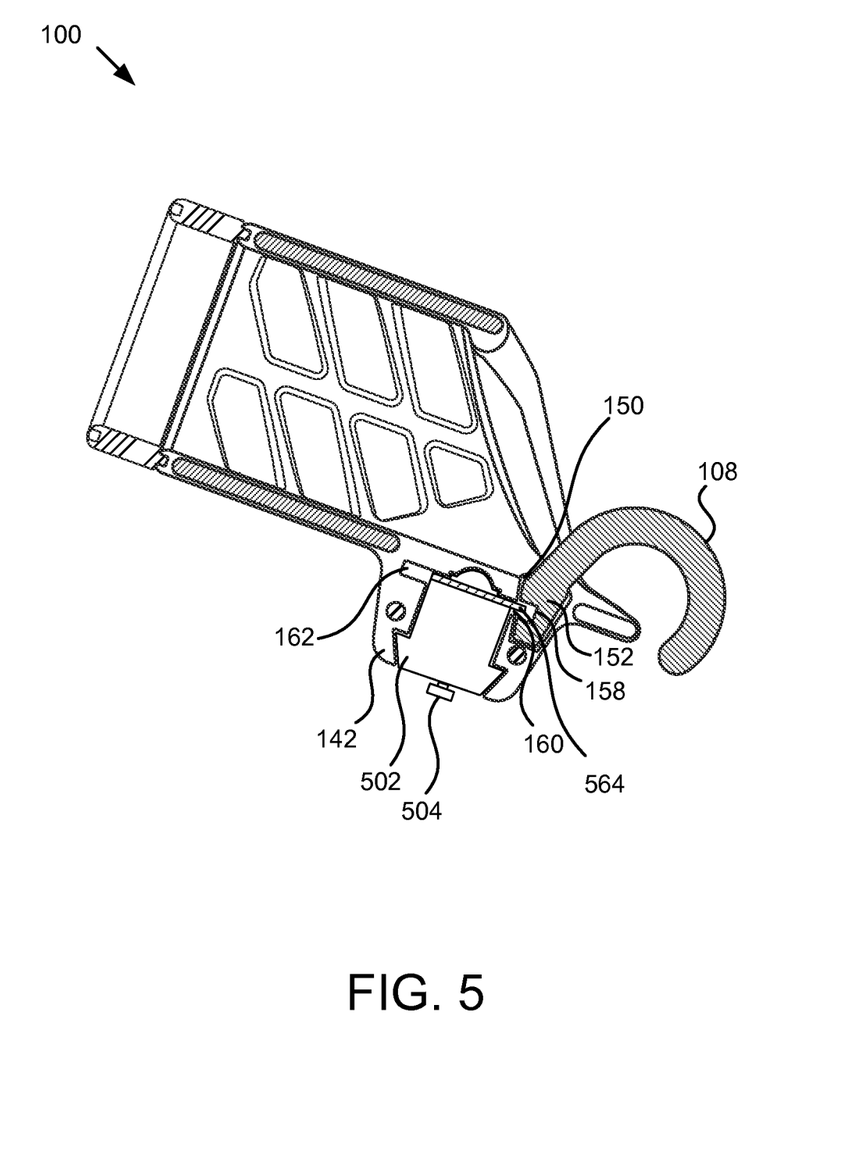
FIG. 5 is a cutaway view illustrating an embodiment taken of the male chastity device taken along line C-C of FIG. 4 in accordance with the present invention.

FIG. 5 illustrates a cutaway view of the male chastity apparatus 100 taken along line C-C of FIG. 4. The male chastity apparatus 100 illustrated in FIG. 5 has the insertion member 152 of the protrusion 108 disposed within the recess 150. The insertion member 152 is disposed within the recess 150 to a depth sufficient to align the slot 158 in the insertion member 152 with the slot 160 in the recess 150. The slot 160 in the recess 150 is in communication with the slot 162 in the lock lobe 142 which allows a flange 564 on the lock 502 to rotate within the slot 160 to retain the insertion member 152 within the recess 150. In this manner the protrusion 108 cannot be removed from within the recess 150 without rotating the flange 564 radially to disengage the slot 158 on the insertion member 152. In the embodiment illustrated in FIG. 5, the lock 502 includes a keyless lock that has a lever 504 to manually unlock the lock 502. In such an embodiment the user may disengage the lock 502 himself without the aid of the key. Such embodiments may be particularly useful where the male chastity apparatus 100 is worn as a decorative item rather than as a chastity device. In other embodiments, the lock 502 may include a key (not shown) that may be removed from the lock so that the user cannot remove the male chastity apparatus 100 without approval of the key holder.

Figure 6A:
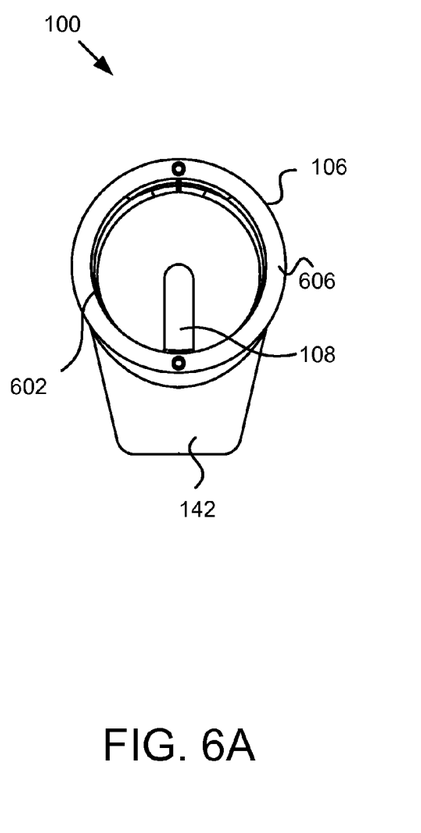
FIG. 6A is an end on view illustrating one embodiment looking down the proximal end of the male chastity device in accordance with the present invention.
Figure 6B:
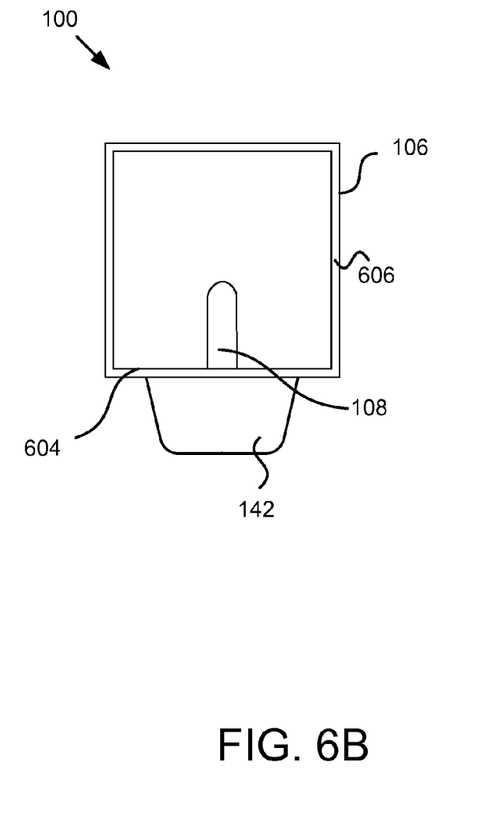
FIG. 6B is an end on view illustrating another embodiment looking down the proximal end of the male chastity device in accordance with the present invention.

FIGS. 6A and 6B illustrate an end on view looking down the center of a male chastity apparatus 100 from the proximal end 118. The illustrations show the housing 106 with the lock lobe 142 and the protrusion 108 disposed within the recess (not shown). In certain embodiments the protrusion 108 is positioned in the center of the housing 106. In other embodiments, such as where the user has alternative piercings other than a Prince Albert piercing, the protrusion 108 may be located adjacent to the position of the piercing on the user's penis when the user is wearing the male chastity apparatus 100.

In the embodiment illustrated in FIG. 6A the housing 106 is cylindrical, conforming to the shape of an average user's penis. In certain embodiments the housing 106 may comprise a different shape other than a cylinder such as a square as illustrated in FIG. 6B. One of skill in the art will recognize that any shape configured to retain the user's penis is within the scope of the present invention.

In certain embodiments the housing 106 maybe offered for sale with different inner diameters 602 according to the average circumference of a user's penis. In a preferred embodiment the sizes offered for sale may include a housing 106 with an inner diameter 602 of 1", 1 and ⅛" or 1 and ¼". One of skill in the art will recognize that other inner diameter 602 sizes are within the scope of the present invention. In certain embodiments the inner diameter 602 of the housing 106 may be sized to snuggly encompass the shaft of the user's penis such that the housing 106 is in constant contact with the shaft of the user's penis around the entire circumference of the inner diameter 602 of the housing 106. In one embodiment, the housing 106 may be sized such that the distance between the inner diameter 602 of the housing 106 and the shaft of the user's penis is approximately one eight of an inch when the user stretches the user's penis away from the user's body. In such an embodiment the gap between the inner diameter 602 of the housing 106 and the shaft of the user's penis may provide access to the shaft of the user's penis for cleaning and hygiene. One of skill in the art will recognize that in certain embodiments it may be desirable to increase the gap between the shaft of the user's penis and the inner diameter 602 of the housing 106. Where the apparatus 100 is used as a chastity device, care should be taken to limit the gap between the shaft of the user's penis and the inner diameter 602 of the housing 106 to a size that allows for cleaning the user's penis while limiting manual stimulation of the user's penis.

In the embodiment illustrated in FIGS. 6A and 6B, the inner diameter 602 or inner surface 604 of the housing 106 may be sized according to common penis sizes. Thus, where the housing 106 is a shape other than a cylinder, such as the embodiment illustrated in FIG. 6B, the size of the inner surface 604 may be adjusted according to the circumference of the user's penis.

In the embodiments illustrated in FIGS. 6A and 6B the distal ridge 606 of the housing 106 may be contoured for comfort. Thus, in certain embodiments the distal ridge 606 is rounded as this is the area that may contact the user's pubic area. Where an extension ring 112 is used, the extension ring 112 may likewise be contoured for comfort on the side that comes in contact with the pubic area of the user.

Figure 7A:
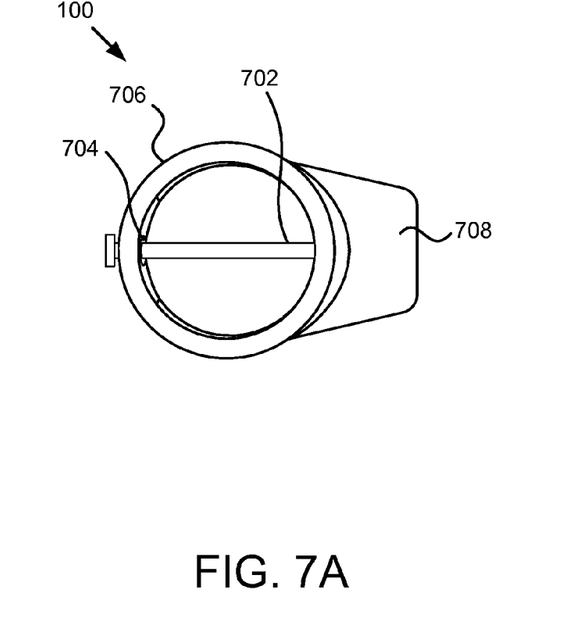
FIG. 7A is an end on view illustrating another embodiment of a male chastity device having a substantially straight protrusion disposed through the housing of the device.
Figure 7B:
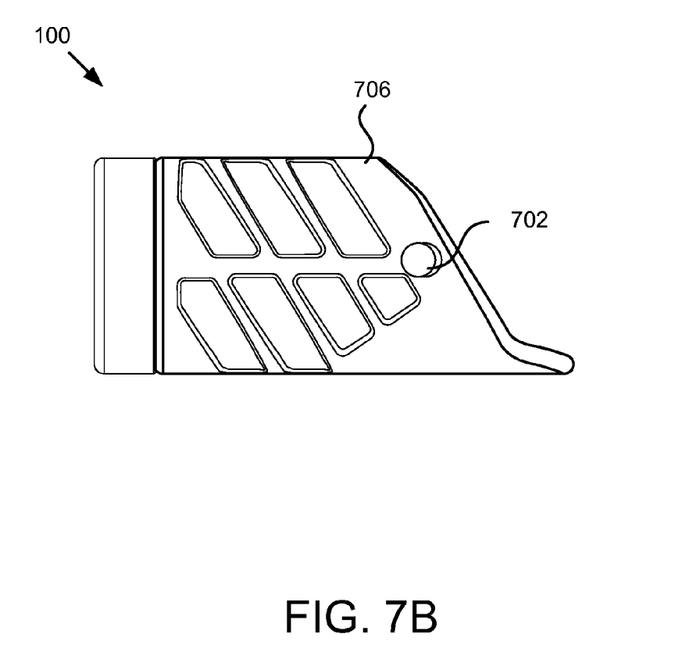
FIG. 7B is a right side view further illustrating one embodiment of the male chastity device of FIG. 7A in accordance with the present invention.

FIGS. 7A and 7B illustrate another embodiment of a male chastity apparatus 100. As discussed above, in certain embodiments the user may have a piercing other than a Prince Albert piercing. For example, in certain embodiments the user may have an ampallang piercing wherein the piercing is made horizontally through the glans of the user's penis. In such a circumstance the protrusion 702 may be a straight bar that is inserted horizontally through the housing 706 at a right angle to the user's penis. In certain embodiments a lock lobe 708 may be positioned adjacent to the position of the user's piercing. Thus, in certain embodiments the lock lobe 708 may be positioned on the side of the housing 706. In one embodiment a hole 704 may be disposed through the housing 706 at a position opposite the lock lobe 708. To lock the male chastity apparatus 100 to the user, the protrusion 702 may be inserted through the hole 704, through the user's ampallang piercing, and into a recess (not shown) that communicates with the lock lobe 708 in a manner similar to that discussed above. In certain embodiments the lock lobe 708 includes a lock that operates to engage an insertion member (not shown) and lock the protrusion 702 to the housing 706. In another embodiment the lock lobe 708 may be omitted and the protrusion 702 may be configured to extend through both sides of the housing 706. In such an embodiment the protrusion 702 may include a hole configured to receive the shackle of a lock in a manner similar to the embodiment discussed above with reference to FIG. 3.

One of skill in the art will recognize that in embodiments where the user's piercing is disposed vertically through the user's penis, the hole 704 and lock lobe 708 may be oriented such that the protrusion 702 is inserted vertically through the housing 706. Similarly, one of skill in the art will recognize that in certain embodiments the user's piercing may be positioned closer to the user's body. In such an embodiment the hole 704 and lock lobe 708 may be positioned closer to the users body to accommodate such a piercing. In one embodiment, the housing 706 may include multiple holes 704 and lock lobes 708 to accommodate a user with multiple piercings.

Figure 8A:
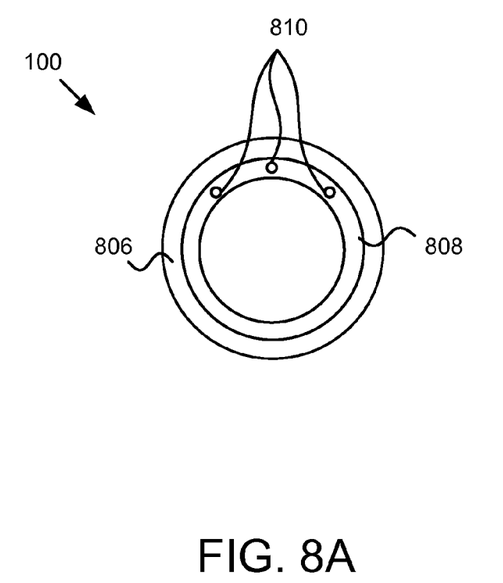
FIG. 8A is an end on view illustrating another embodiment of a male chastity device having at least one recess for receiving a protrusion with the at least one recess oriented to accommodate a user's dydoe piercing.
Figure 8B:
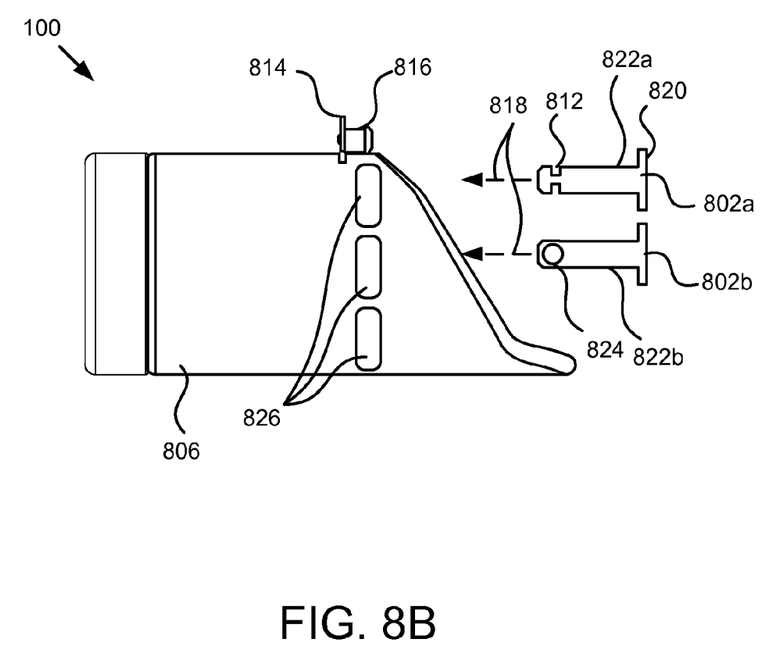
FIG. 8B is a right side view further illustrating one embodiment of the male chastity device of FIG. 8A in accordance with the present invention.

FIGS. 8A and 8B illustrate another embodiment of a male chastity apparatus 100. As discussed above, in certain embodiments the user may have a dydoe piercing wherein the piercing is made through ridge of the user's glans. In such an embodiment the housing 806 of the male chastity apparatus 100 may include an inner shelf 808 that rests behind the ridge of the user's glans when the housing 806 is worn by the user. In certain embodiments the inner shelf 808 may be shaped to contour to the ridge of the user's glans. The inner shelf 808 includes at least one recess 810 that is configured to receive a protrusion 802a. While the embodiment illustrated in FIG. 8A includes three recesses 810, one of skill in the art will recognize that the current invention is not limited to three recesses 810.

As depicted in FIG. 8B, the protrusion 802a may include a fastening slot 812 that locks the protrusion 802a within the recess 810 on the inner shelf 808. In use, once the user's penis is placed within the housing 806 to a position sufficient to allow the ridge of the user's glans to rest against the inner shelf 808 of the housing 806, the protrusion 802a is inserted through the user's dydoe piercing and into the recess 810 in the direction of arrows 818. Once the protrusion 802a is inserted into the at least one recess 810 the fastening slot 812 of the protrusion 802a is engaged by a locking flange 814 on a lock 816. In certain embodiments the lock 816 may be enclosed within a lock lobe (not shown). The head 820 of the protrusion 802a may be substantially larger than the shaft 822a of the protrusion 802a to ensure that the user cannot simply slip the end of the protrusion 802a off of the dydoe piercing.

In another embodiment, such as the embodiment depicted by the protrusion 802b, a hole 824 may be disposed through the shaft 822b of the protrusion 802b. In such an embodiment a shank of a lock (not shown) may engage the hole 824 in the protrusion 802b. In certain embodiments, such as where a lock having a shank is used to secure the protrusion 802b to the housing 806, the housing 806 may include one or more locking access holes 826 that are sized to allow access through the housing 806 to secure the protrusion 802b to the housing 806.

Figure 9:
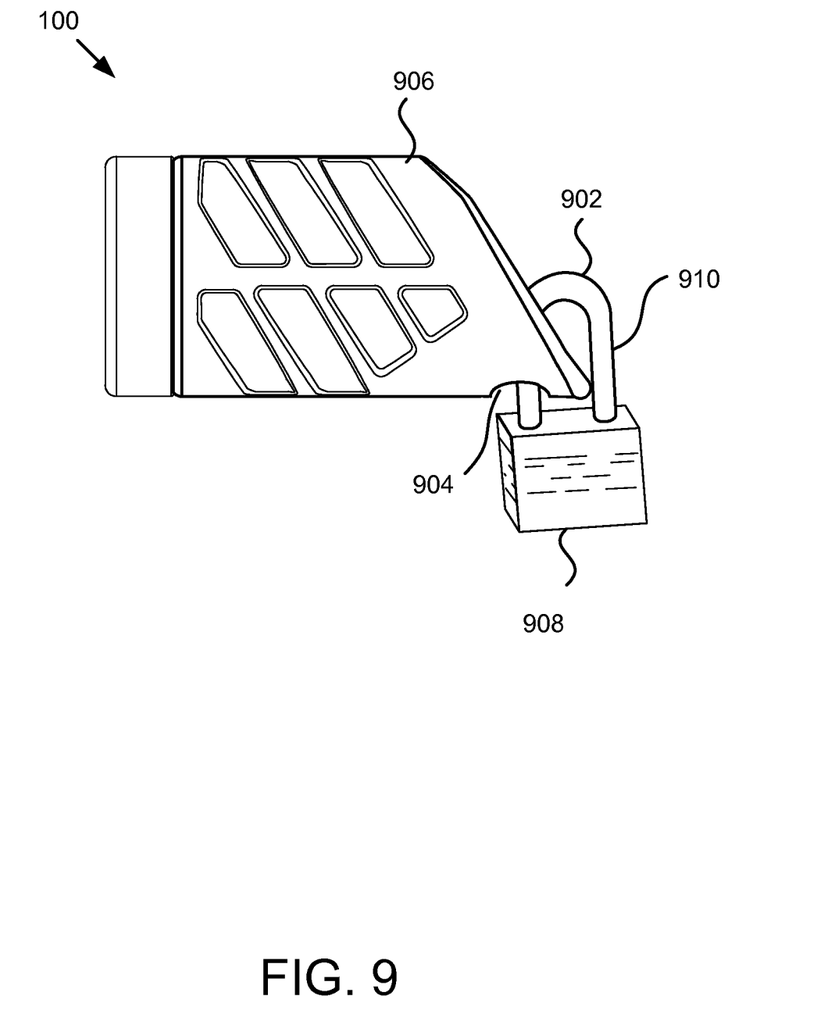
FIG. 9 is a right side view illustrating a male chastity device with a lock attached.

FIG. 9 illustrates another embodiment of a male chastity apparatus 100 that includes a housing 906, a protrusion 902, and a lock 908. The housing 906, in certain embodiments, is made of a substantially rigid material. The housing 906 may encompass the user's penis in a manner substantially similar to the embodiments described above. In the embodiment illustrated in FIG. 9, the housing 906 includes a recess 904 for receiving the protrusion 902.

In certain embodiments the protrusion 902 may be the shank 910 of the lock 908. In operation, the protrusion 902 may be placed through a user's piercing, through the recess 904 in the housing 906, and then locked to the housing 906 with lock 908 to rigidly attach the protrusion 902 to the housing 906. In this manner, housing 906 is rigidly attached to the user and prevents unauthorized manual stimulation of the shaft of the user's penis.

One of skill in the art will recognize that in certain embodiments the lock 908 may be available in a variety of sizes, both in regard to the gauge as well as the radius of the protrusion 902 to accommodate different locations for a user's piercing. For example, as discussed above, a user with a Prince Albert piercing near the end of the glans of his penis can use a lock 908 having a protrusion 902 with a relatively small radius. Other users may require the protrusion 902 to have a larger radius where the Prince Albert piercing is located further back on the glans of the user's penis.

Figure 10:
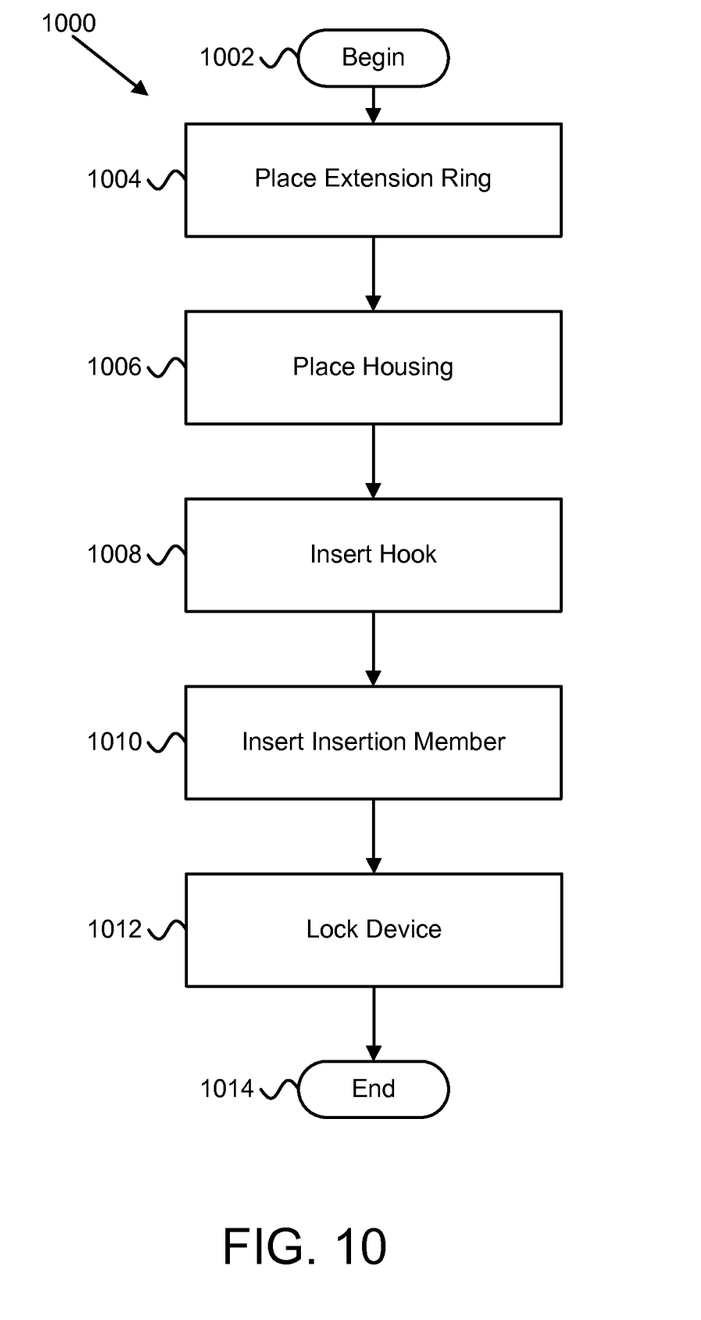
FIG. 10 is a schematic flow chart diagram illustrating an embodiment of a method of ensuring male chastity in accordance with the present invention.

FIG. 10 illustrates a method 1000 for ensuring male chastity according to the present invention. The male chastity apparatus 100 described above may be used in the method 1000.

The method begins 1002 and in block 1004 an extension ring 112 is placed on the user's penis. In certain embodiments the extension ring 112 may be unnecessary due to the length of the user's penis. In other embodiments the extension ring 112 may be glued to the housing 106 before the user places either the extension ring 112 or the housing 106 on his penis. In such an embodiment the steps in block 1004 and 1006 may be combined to a single step of placing the combined housing 106 and extension ring 112 onto the user's penis.

Where the housing 106 and the extension ring 112 are not combined, only the housing 106 is placed on the user's penis in block 1006. In certain embodiments the user may wish to lubricate the penis before inserting the penis into either the housing 106 or the extension ring 112. In certain embodiments the user selects a housing 106 size that leaves a gap of one eighth to one fourth of an inch between the user's penis and the inner diameter 602 or the inner surface 604 of the male chastity apparatus 100 when the user's penis is stretched away from the user's body.

At block 1008 the protrusion 108 is placed through a user's piercing. As discussed above, in certain embodiments the user's piercing is a Prince Albert piercing in which the piercing enters the user's penis on the underside of the penis just below the glans of the penis and exits the penis through the urinary tract. One of skill in the art will recognize that in other embodiments the protrusion 108 may be placed through other piercings.

At block 1010 the insertion member 152 is inserted into the recess 150 of the housing 106. The user may wish to adjust the housing 106 right or left, forward or backward to align the slot 158 in the insertion member 152 with the slot 160 in the recess 150.

At block 1012 the device is locked by turning the lock 110 to slide the flange 164 of the lock 110 into the slot 158 in the insertion member 152. Where a keyed lock 110 is used the key is removed from the lock 110 and the method ends 1014.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:
1. A male chastity apparatus comprising:
 a housing comprising an at least partial enclosure elongated in a lengthwise direction and configured to contain at least a portion of a shaft of a penis of a user, the housing comprising a substantially rigid material that prevents stroking of the shaft of the penis by the user;
a protrusion configured to engage a piercing in the penis of the user, the protrusion comprising a substantially rigid material; and
a lock configured to engage the protrusion, the lock attaching the protrusion to the housing.

2. The apparatus of claim 1, further comprising a recess disposed within the housing, the recess configured to receive a proximal end of the protrusion, wherein the proximal end of the protrusion comprises an insertion member configured to engage the recess of the housing.

3. The apparatus of claim 2, wherein a cross section of the recess is substantially oval shaped and wherein a cross section of the insertion member of the protrusion is substantially oval shaped such that rotation of the protrusion is minimized when the insertion member is disposed within the recess.

4. The apparatus of claim 2, further comprising a lock lobe disposed on the housing, wherein the recess communicates with the lock lobe such that the insertion member of the protrusion is at least partially disposed within the lock lobe.

5. The apparatus of claim 4, wherein the insertion member includes a slot transecting the insertion member, wherein the lock lobe includes a slot coincident to the slot on the insertion member, the lock comprising a locking flange, wherein the locking flange is configured to engage the slot on the insertion member in a first position and disengage the slot on the insertion member in a second position.

6. The apparatus of claim 1, wherein a distal end of the protrusion is shaped as a partial ring, the partial ring having a radius sufficient to clear an end of a glans of the penis of the user when the protrusion is engaged in a Prince Albert piercing of the user.

7. The apparatus of claim 1, further comprising a recess disposed within the housing, wherein the protrusion comprises a shank of the lock, the recess configured to receive the shank of the lock to rigidly attach the protrusion to the housing.

8. The apparatus of claim 1, wherein the housing comprises a flange extending from a distal end on a bottom of the housing, wherein the flange of the housing is configured to engage the protrusion at a distal end of the protrusion such that the distal end of the protrusion and the flange of the housing cooperating to prevent removal of the housing from the shaft of the user's penis.

9. The apparatus of claim 1, wherein a top of the housing is shorter than a bottom of the housing and wherein a distal end of the housing is sloped from the bottom of the housing to the top of the housing such that the distal end of the housing is contoured to the shape of a glans of the user's penis.

10. The apparatus of claim 1, wherein the housing comprises at least one access vent, the at least one access vent sized to receive a cleaning utensil.

11. The apparatus of claim 1, further comprising an extension ring, the extension ring configured to engage the housing to extend a length of the housing.

12. A male chastity apparatus, the apparatus comprising:
a housing configured to contain a shaft of a penis of a user, the housing comprising a substantially rigid material that prevents stroking of the shaft of the penis by the user;
a protrusion configured to engage a piercing in the penis of the user, the protrusion comprising a substantially rigid material;
a recess disposed within the housing, the recess configured to receive a proximal end of the protrusion, wherein the proximal end of the protrusion comprises an insertion member configured to engage the recess of the housing;
a lock configured to engage the protrusion, the lock attaching the protrusion to the housing.

13. The apparatus of claim 12, further comprising a lock lobe disposed on the housing, wherein the recess communicates with a lock lobe such that the insertion member of the protrusion is at least partially disposed within the lock lobe.

14. The apparatus of claim 13, wherein the insertion member includes a slot transecting the insertion member, wherein the lock lobe includes a slot coincident to the slot on the insertion member, the lock comprising a locking flange, wherein the locking flange is configured to engage the slot on the insertion member in a first position and disengage the slot on the insertion member in a second position.

15. The apparatus of claim 12, wherein a cross section of the recess is substantially oval shaped and wherein a cross section of the insertion member of the protrusion is substantially oval shaped such that rotation of the protrusion is minimized when the insertion member is disposed within the recess.

16. The apparatus of claim 12, wherein the housing comprises at least one access vent, the at least one access vent sized to receive a cleaning utensil.

17. The apparatus of claim 12, further comprising an extension ring, the extension ring configured to engage the housing to extend the length of the housing.

18. A method of facilitating male chastity, the method comprising:
placing a housing on a shaft of a penis of a user, the housing comprising a substantially rigid material that prevents stroking of the shaft of the penis by the user;
placing a protrusion through a piercing in the penis of the user, the protrusion configured to engage the piercing in the penis of the user, the protrusion comprising a substantially rigid material;
inserting the protrusion in a recess disposed in the housing; and
locking the protrusion in the recess of the housing with a lock, the lock attaching the protrusion to the housing.

19. The method of claim 18, wherein a distal end of the protrusion comprises a partial ring, the partial ring having a radius sufficient to clear an end of a glans of a penis of the user when the protrusion is engaged in a user's Prince Albert piercing.

20. The method of claim 18, further comprising extending the length of the housing by adding an extension ring to an end of the housing, the extension ring configured to engage the housing to extend the length of the housing.

* * * * *